US012780810B2

(12) United States Patent
Kolesa et al.

(10) Patent No.: US 12,780,810 B2
(45) Date of Patent: Nov. 3, 2026

(54) SOLID STATE FORMS OF N-[2-(2-{4-[2-(6,7-DIMETHOXY-3, 4-DIHYDRO-2(1H)-ISOQUINOLINYL) ETHYL]PHENYL}-2H- TETRAZOL-5-YL)-4,5-DIMETHOXYPHENYL]-4-OXO-4H-CHROMENE-2-CARBOXAMIDE MESYLATE SALT

(71) Applicant: ASSIA CHEMICAL INDUSTRIES LTD., Tel Aviv (IL)

(72) Inventors: Pavel Kolesa, Hlubocec (CZ); Miroslav Vavrecka, Ostrava (CZ); Roman Gabriel, Olomouc (CZ); Martin Valik, Male Hostice (CZ)

(73) Assignee: ASSIA CHEMICAL INDUSTRIES LTD., Tel Aviv (IL)

( * ) Notice: Subject to any disclaimer, the term of this patent is extended or adjusted under 35 U.S.C. 154(b) by 712 days.

(21) Appl. No.: 18/014,359

(22) PCT Filed: Jul. 9, 2021

(86) PCT No.: PCT/US2021/041028
§ 371 (c)(1),
(2) Date: Jan. 4, 2023

(87) PCT Pub. No.: WO2022/011221
PCT Pub. Date: Jan. 13, 2022

(65) Prior Publication Data

US 2023/0278990 A1 Sep. 7, 2023

Related U.S. Application Data

(60) Provisional application No. 63/158,934, filed on Mar. 10, 2021, provisional application No. 63/057,959, filed on Jul. 29, 2020, provisional application No. 63/050,178, filed on Jul. 10, 2020.

(51) Int. Cl.

| | |
|---|---|
| ***C07D 405/14*** | (2006.01) |
| ***A61K 31/337*** | (2006.01) |
| ***A61K 31/4725*** | (2006.01) |

(52) U.S. Cl.
CPC .......... *C07D 405/14* (2013.01); *A61K 31/337* (2013.01); *A61K 31/4725* (2013.01); *C07B 2200/13* (2013.01)

(58) Field of Classification Search
CPC ................ C07D 405/14; A61K 31/337; A61K 31/4725; C07B 2200/13
See application file for complete search history.

(56) References Cited

U.S. PATENT DOCUMENTS

| | | | |
|---|---|---|---|
| 7,625,926 | B2 | 12/2009 | Bang et al. |
| 2014/0148602 | A1 | 5/2014 | Bang et al. |

FOREIGN PATENT DOCUMENTS

| | | | | |
|---|---|---|---|---|
| WO | WO-2014092489 | A1 * | 6/2014 | .............. A61P 43/00 |
| WO | WO-2020168144 | A1 * | 8/2020 | ............. A61K 45/06 |
| WO | 2020194175 | A1 | 10/2020 | |
| WO | 2021044350 | A1 | 3/2021 | |

OTHER PUBLICATIONS

Lee, et al.; Annual Review of Chemical and Biomolecular Engineering, v2, pp. 259-280; 2011 (Year: 2011).*
Mino R Caira, “Crystalline Polymorphism of Organic Compounds”, Topics in Current Chemistry, vol. 198, p. 163-208 (Jan. 1, 1998).
International Search Report and Written Opinion of the International Searching Authority issued in corresponding application PCT/US2021/041028 mailed Nov. 19, 2021 (18 pages).

* cited by examiner

*Primary Examiner* — Jeffrey S Lundgren
*Assistant Examiner* — W. Justin Youngblood
(74) *Attorney, Agent, or Firm* — Carter, DeLuca & Farrell LLP

(57) ABSTRACT

The present disclosure relates to solid state forms of Encequidar and Encequidar mesylate, processes for their preparation, and pharmaceutical compositions thereof.

13 Claims, 9 Drawing Sheets

Figure 1. A powder X-ray diffraction pattern ("powder XRD" or "PXRD") of Encequidar mesylate Form K.
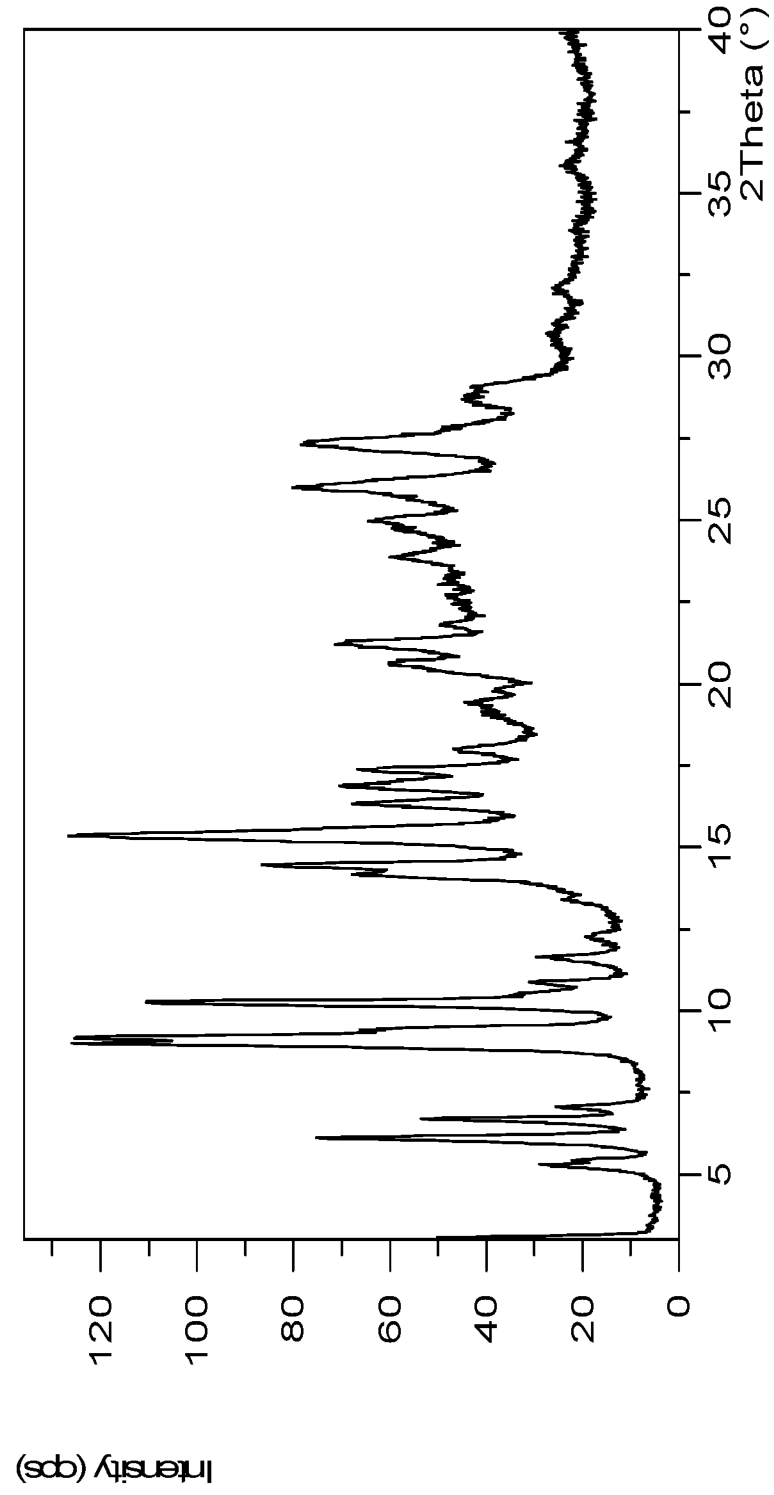

Figure 2. A PXRD of crystalline Encequidar mesylate Form L.
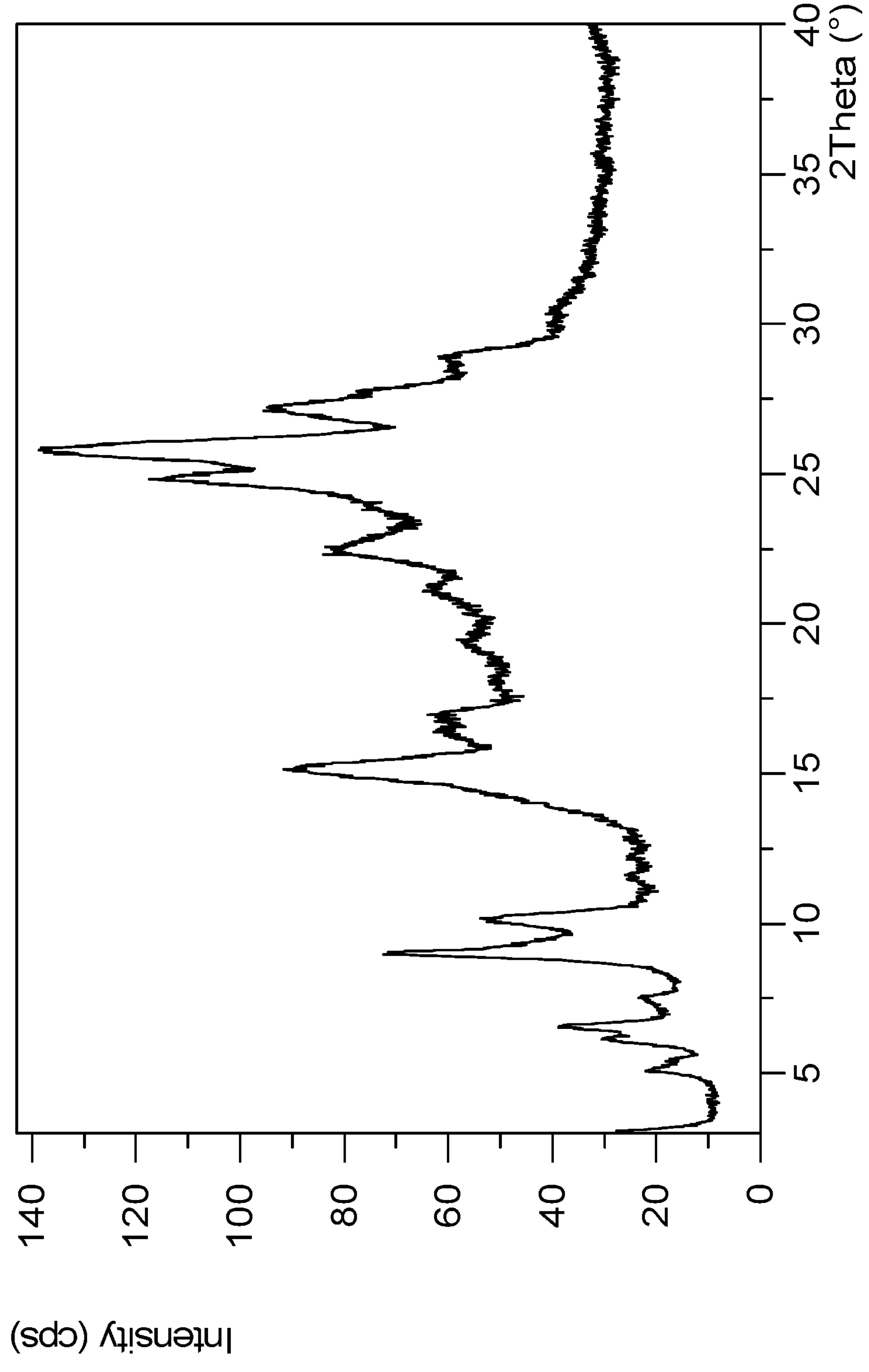

Figure 3. A PXRD of crystalline Encequidar mesylate Form M.
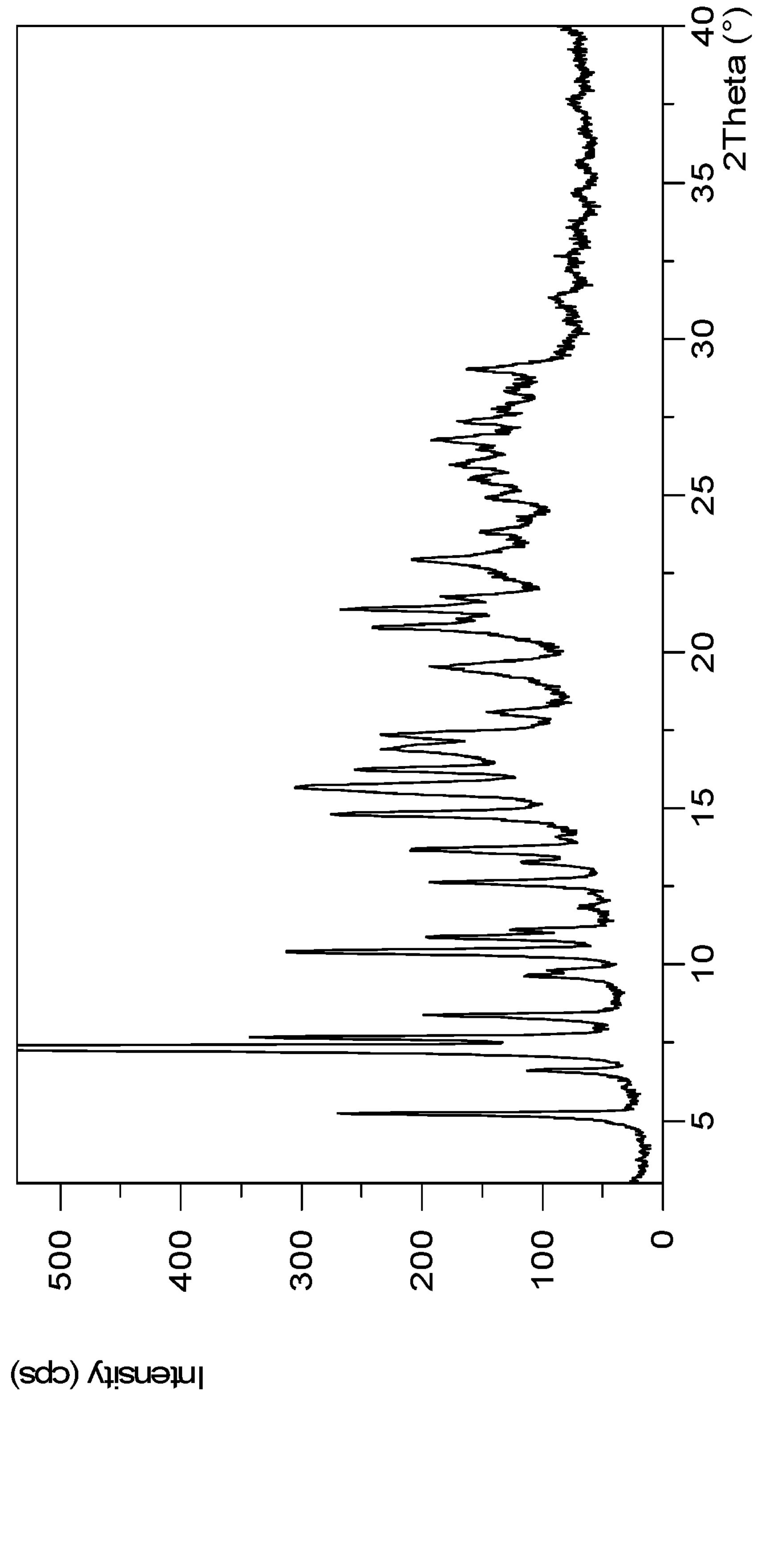

Figure 4. A PXRD of crystalline Encequidar Form IV.
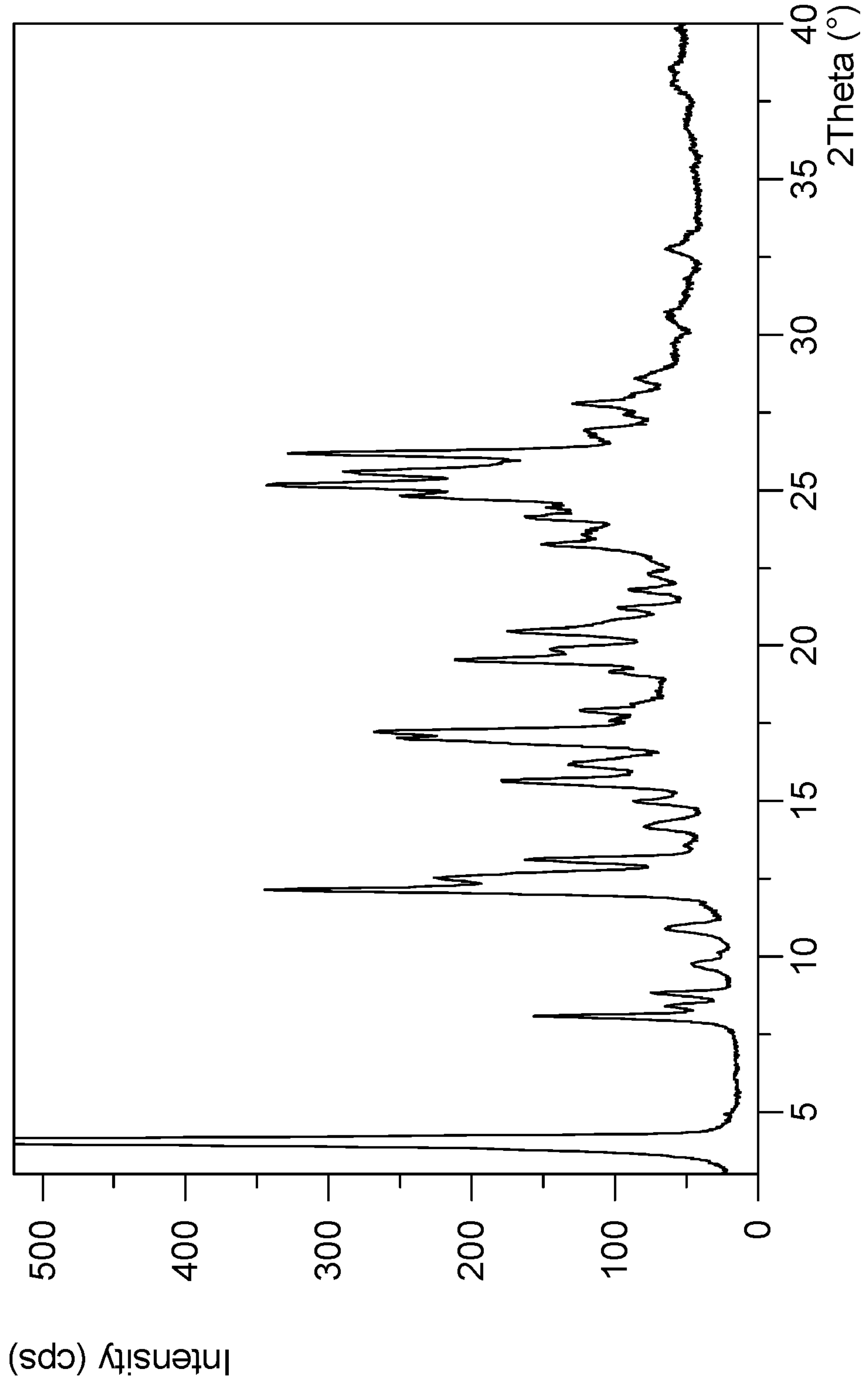

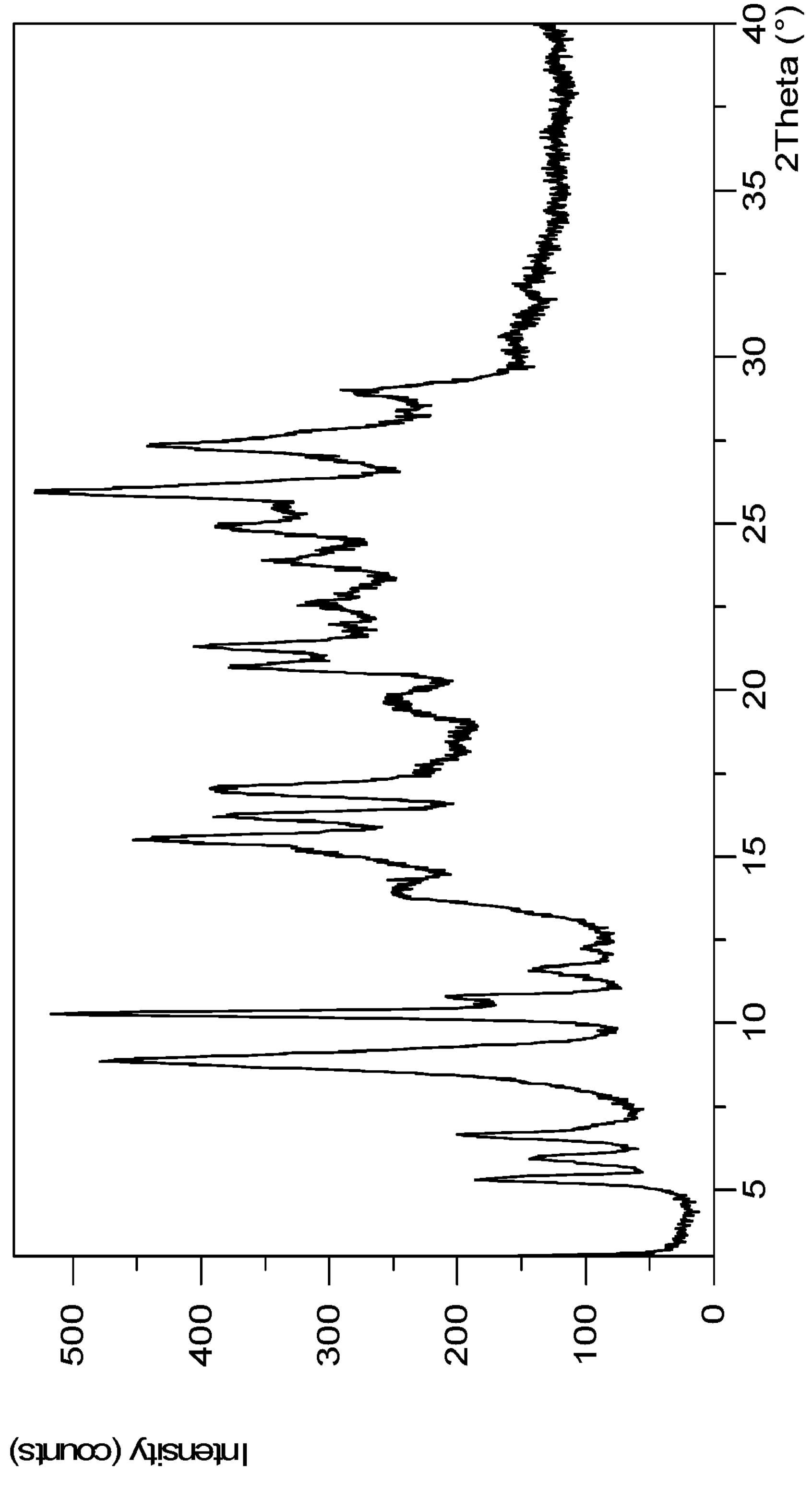
Figure 5. A powder X-ray diffraction pattern of Encequidar mesylate Form K, prepared according to Example 4.

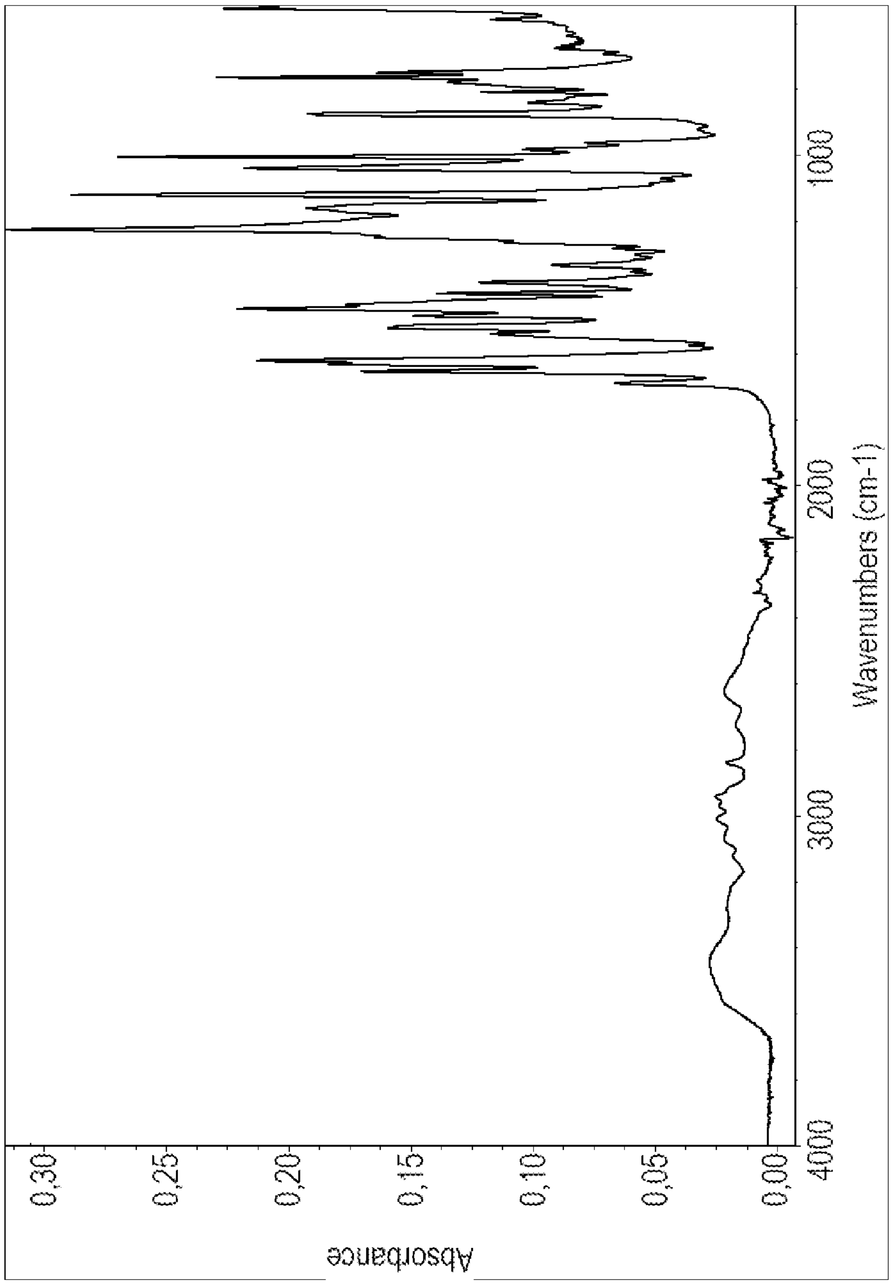
Figure 6. A FT-IR spectrum of Encequidar Mesylate Form K.

Figure 7: $^{13}C$ solid state NMR spectrum (range from 200-0 ppm) of Encequidar Mesylate Form K.
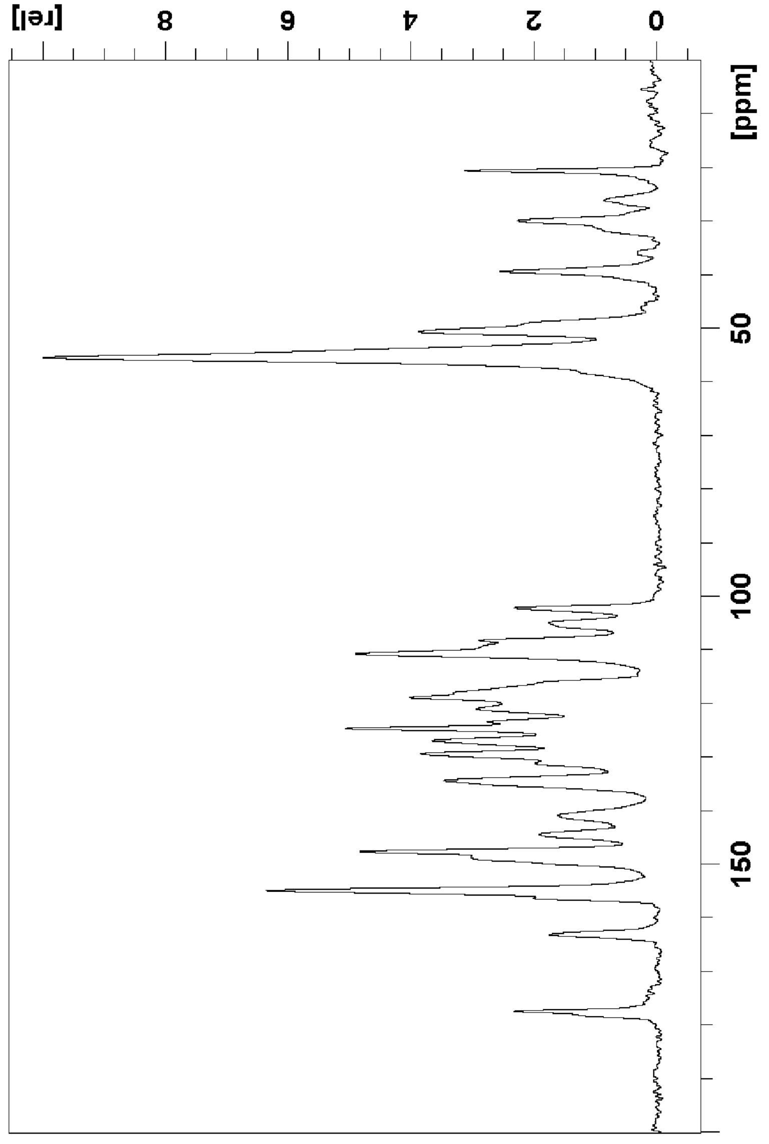

Figure 8: $^{13}C$ solid state NMR spectrum (range from 200-100 ppm) of Encequidar Mesylate Form K.
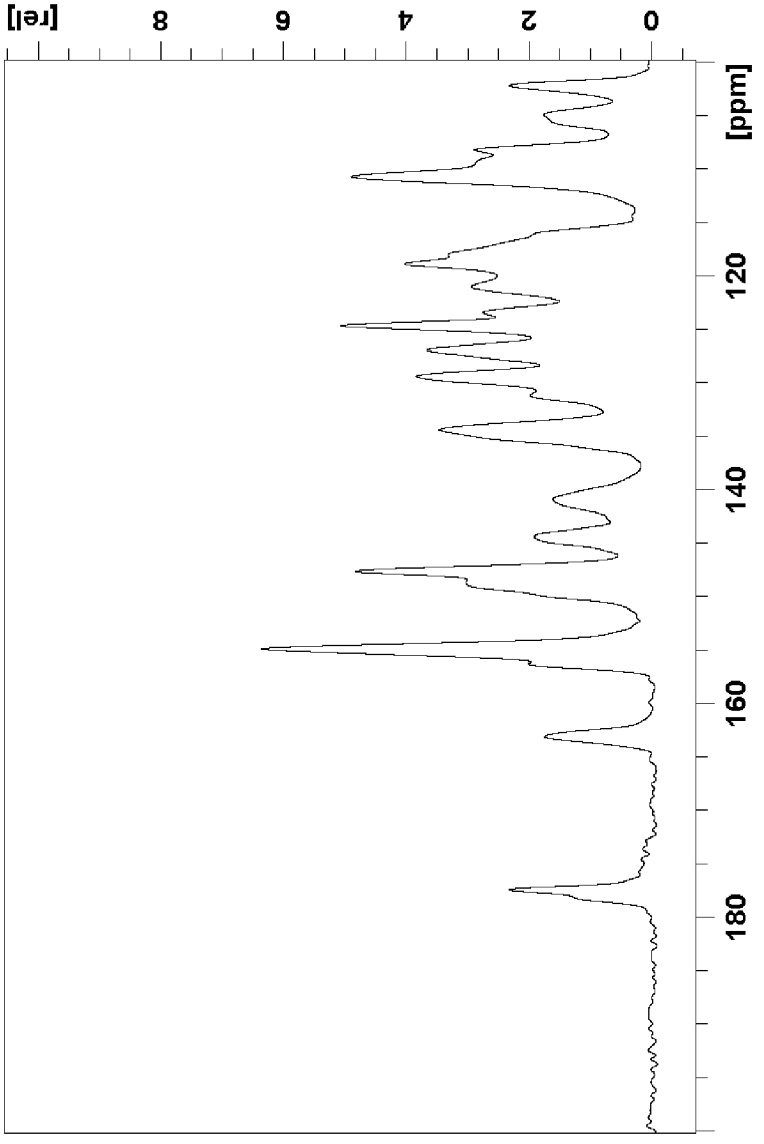

Figure 9: $^{13}C$ solid state NMR spectrum (range from 100-0 ppm) of Encequidar Mesylate Form K.
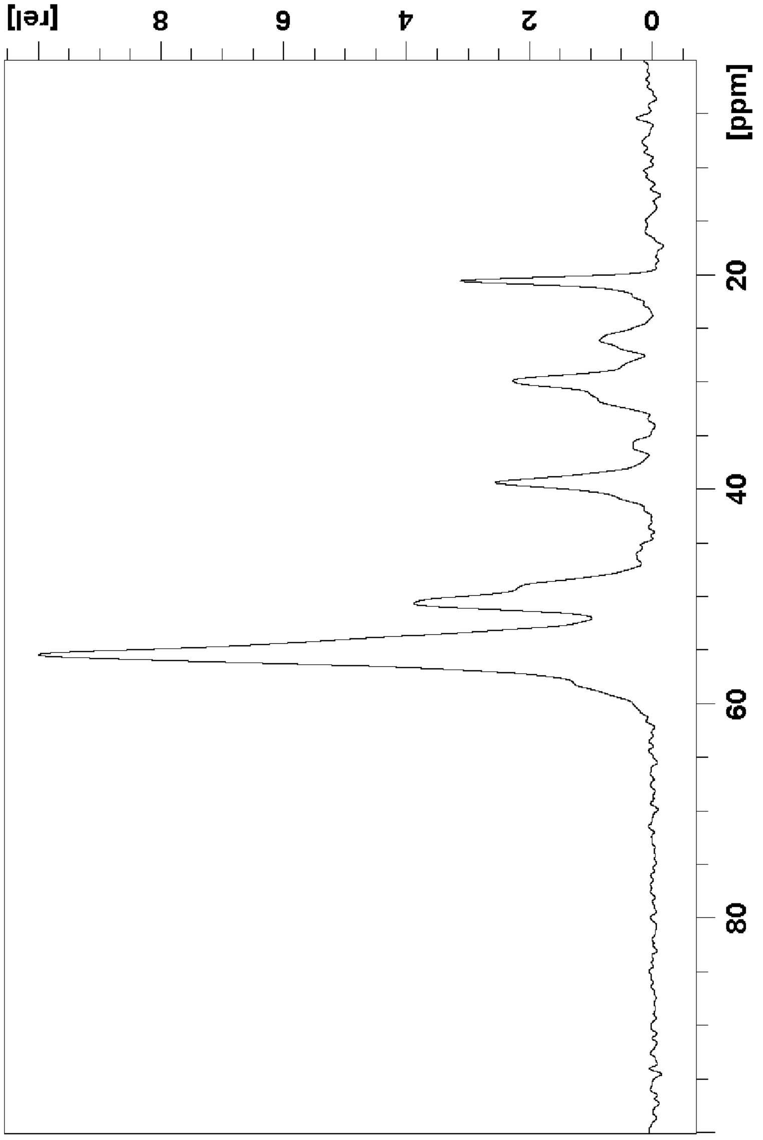

SOLID STATE FORMS OF N-[2-(2-{4-[2-(6,7-DIMETHOXY-3,4-DIHYDRO-2(1H)-ISOQUINOLINYL)ETHYL]PHENYL}-2H-TETRAZOL-5-YL)-4,5-DIMETHOXYPHENYL]-4-OXO-4H-CHROMENE-2-CARBOXAMIDE MESYLATE SALT

CROSS REFERENCE TO RELATED APPLICATIONS

This application is a National Stage of, and claims priority to and the benefit of, International Patent Application No. PCT/US2021/041028, filed Jul. 9, 2021, which, in turn, claims the benefit of and priority to, U.S. Provisional Application No. 63/050,178, filed Jul. 10, 2020; U.S. Provisional Application No. 63/057,959 filed Jul. 29, 2020; and U.S. Provisional Application No. 63/158,934, filed Mar. 10, 2021, the entire disclosures of each of which are incorporated by reference herein.

TECHNICAL FIELD

The present disclosure relates to solid state forms of Encequidar and Encequidar (HM-30181A) mesylate, processes for their preparation, and pharmaceutical compositions thereof.

BACKGROUND

Encequidar has the chemical name N-[2-(2-{4-[2-(6,7-Dimethoxy-3,4-dihydro-2(1H)-isoquinolinyl)ethyl]phenyl}-2H-tetrazol-5-yl)-4,5-dimethoxyphenyl]-4-oxo-4H-chromene-2-carboxamide, and the code name HM-30181A. Encequidar (HM-30181A) has the following chemical structure:

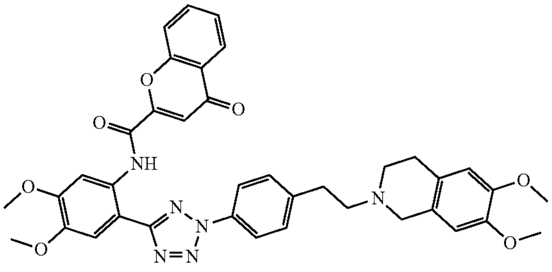

Or the following, as Encequidar mesylate in a hydrate form:

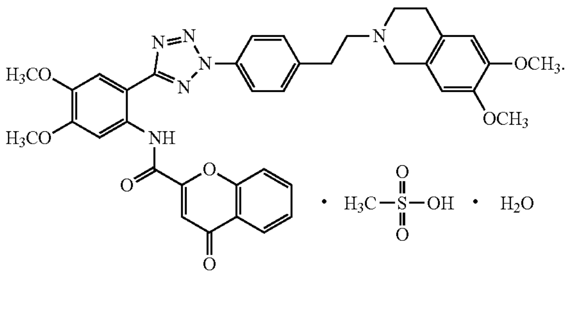

Encequidar (HM-30181A) is being developed as a combination with Paclitaxel, indicated for the treatment of metastatic breast cancer and gastric cancer. Encequidar (HM-30181A) is disclosed in U.S. Pat. No. 7,625,926 (counterpart of International Publication No. WO 2005/033097). International Publication No. WO 2011/087316 discloses a process for preparing Encequidar (HM-30181A) and its mesylate salt, which includes use of a benzothiazolylthioester in the final acylation step.

Solid state forms of Encequidar (HM-30181A) and its mesylate salt are disclosed in International Publication No. WO 2014/092489. Additional solid state forms and co-crystals of Encequidar and Encequidar Mesylate are described in WO 2020/168144.

Polymorphism, the occurrence of different crystal forms, is a property of some molecules and molecular complexes. A single compound, like Encequidar (HM-30181A) or salt thereof, may give rise to a variety of polymorphs having distinct crystal structures and physical properties like melting point, thermal behaviors (e.g., measured by thermogravimetric analysis—"TGA", or differential scanning calorimetry—"DSC"), powder X-ray diffraction (PXRD) pattern, infrared absorption fingerprint, Raman absorption fingerprint, and solid state ($^{13}C$-) NMR spectrum. One or more of these techniques may be used to distinguish different polymorphic forms of a compound.

Different salts and solid state forms (including solvated forms and co-crystals) of an active pharmaceutical ingredient may possess different properties. Such variations in the properties of different salts and solid state forms, co-crystals and solvates may provide a basis for improving formulation, for example, by facilitating better processing or handling characteristics, improving the dissolution profile, or improving stability (polymorph as well as chemical stability) and shelf-life. These variations in the properties of different salts and solid state forms may also provide improvements to the final dosage form, for instance, if they serve to improve bioavailability. Different salts and solid state forms, co-crystals and solvates of an active pharmaceutical ingredient may also give rise to a variety of polymorphs or crystalline forms, which may in turn provide additional opportunities to use variations in the properties and characteristics of a solid active pharmaceutical ingredient for providing an improved product.

Discovering new salts, solid state forms, co-crystals and solvates of a pharmaceutical product can provide materials having desirable processing properties, such as ease of handling, ease of processing, storage stability, and ease of purification, or as desirable intermediate crystal forms that facilitate conversion to other salts or polymorphic forms. New salts, polymorphic forms, co-crystals and solvates of a pharmaceutically useful compound can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life.

SUMMARY

The present disclosure relates to solid state forms of Encequidar and Encequidar mesylate, processes for preparation, and to pharmaceutical compositions thereof.

The present disclosure also provides uses of the solid state forms of Encequidar and Encequidar mesylate or combination thereof for preparing other solid state forms of Encequidar and Encequidar mesylate.

In another embodiment, the present disclosure encompasses the herein described solid state forms of Encequidar and Encequidar mesylate for use in the preparation of pharmaceutical compositions and/or formulations, particularly as a combination with additional active agents, such as Paclitaxel, in some embodiments for the treatment of cancer, or in some embodiments, for the treatment of metastatic breast cancer and/or gastric cancer.

Another embodiment of the present disclosure encompasses the use of the herein described solid state forms of Encequidar and Encequidar mesylate for the preparation of pharmaceutical compositions and/or formulations. The pharmaceutical compositions and/or formulations can be in combination with additional active agents, such as Paclitaxel.

The present disclosure further provides pharmaceutical compositions including solid state forms of Encequidar and Encequidar mesylate. The pharmaceutical compositions and/or formulations can be in combination with additional active agents, such as Paclitaxel.

In yet another embodiment, the present disclosure encompasses pharmaceutical formulations including combinations of the solid state forms of Encequidar and Encequidar mesylate and at least one pharmaceutically acceptable excipient. The pharmaceutical composition or formulation includes oral dosage forms, e.g., a tablet or capsule, and can be in combination with additional active agents, such as Paclitaxel.

The present disclosure encompasses processes to prepare said pharmaceutical formulations of solid state forms of Encequidar and Encequidar mesylate, including combining any one or a combination of the solid state forms of Encequidar and Encequidar mesylate according to the present disclosure with at least one pharmaceutically acceptable excipient. The process can optionally include adding additional active agent(s).

The solid state forms of Encequidar and Encequidar mesylate, as well as the pharmaceutical compositions or formulations of solid state forms of Encequidar and Encequidar mesylate according to the present disclosure, particularly combinations with additional active agents, such as Paclitaxel, can be used as medicaments, in embodiments for the treatment of cancer, or in embodiments for the treatment of metastatic breast cancer and/or gastric cancer;

The present disclosure also provides methods of treating metastatic breast cancer and/or gastric cancer by administering a therapeutically effective amount of any one or a combination of the solid state forms of Encequidar and Encequidar mesylate according to the present disclosure, or at least one of the above pharmaceutical compositions or formulations, optionally as a combination with additional active agents, such as Paclitaxel, to a subject suffering from cancer, or to a subject suffering from metastatic breast cancer and/or gastric cancer, or otherwise in need of treatment.

The present disclosure also provides uses of solid state forms of Encequidar and Encequidar mesylate of the present disclosure, or at least one of the above pharmaceutical compositions or formulations, for the manufacture of a medicament for treating cancer, or for the manufacture of a medicament for treating metastatic breast cancer and/or gastric cancer. The medicament can be a combination with additional active agents, such as Paclitaxel.

BRIEF DESCRIPTION OF THE FIGURES

FIG. 1 shows a powder X-ray diffraction pattern ("powder XRD" or "PXRD") of Encequidar mesylate Form K.

FIG. 2 shows a PXRD of crystalline Encequidar mesylate Form L.

FIG. 3 shows a powder X-ray diffraction pattern of Encequidar mesylate Form M.

FIG. 4 shows a powder X-ray diffraction pattern of Encequidar Form IV.

FIG. 5 shows a powder X-ray diffraction pattern of Encequidar mesylate Form K, prepared according to Example 4.

FIG. 6 shows a FT-IR spectrum of Encequidar Mesylate Form K.

FIG. 7 shows a $^{13}C$ solid state NMR spectrum (range from 200-0 ppm) of Encequidar mesylate Form K.

FIG. 8 shows a $^{13}C$ solid state NMR spectrum (range from 200-100 ppm) of Encequidar mesylate Form K.

FIG. 9 shows a $^{13}C$ solid state NMR spectrum (range from 100-0 ppm) of Encequidar mesylate Form K.

DETAILED DESCRIPTION

The present disclosure relates to solid state forms of Encequidar and Encequidar mesylate, to processes for preparation thereof, and to pharmaceutical compositions including these solid state forms or combinations thereof.

The solid state forms of Encequidar and Encequidar mesylate according to the present disclosure may have advantageous properties including at least one of: chemical or polymorphic purity, flowability, solubility, dissolution rate, bioavailability, morphology or crystal habit, stability such as chemical stability as well as thermal and mechanical stability with respect to polymorphic conversion, stability towards dehydration and/or storage stability, a lower degree of hygroscopicity, low content of residual solvents and advantageous processing and handling characteristics such as compressibility, or bulk density.

A crystal form may be referred to herein as being characterized by graphical data "as depicted in" a Figure. Such data include, for example, powder X-ray diffractograms and solid state NMR spectra. As is well-known in the art, the graphical data potentially provides additional technical information to further define the respective solid state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Encequidar and Encequidar mesylate referred to herein as being characterized by graphical data "as depicted in" a Figure will thus be understood to include any crystal forms of the Encequidar and Encequidar mesylate, characterized with the graphical data having such small variations, as are well known to the skilled person, in comparison with the Figure.

A solid state form (or polymorph) may be referred to herein as polymorphically pure or substantially free of any other solid state (or polymorphic) forms. As used herein in this context, the expression "substantially free of any other forms" will be understood to mean that the solid state form contains about 20% or less, about 10% or less, about 5% or less, about 2% or less, about 1% or less, or about 0% of any other forms of the subject compound as measured, for example, by PXRD. Thus, solid state forms of Encequidar and Encequidar mesylate described herein as substantially free of any other solid state forms would be understood to contain greater than about 80% (w/w), greater than about 90% (w/w), greater than about 95% (w/w), greater than about 98% (w/w), greater than about 99% (w/w), or about 100% (w/w) of the subject solid state forms of Encequidar and Encequidar mesylate. Accordingly, in some embodiments of the disclosure, the described solid state forms of Encequidar and Encequidar mesylate may contain from about 1% to about 20% (w/w), from about 5% to about 20% (w/w), or from about 5% to about 10% (w/w) of one or more other solid state forms of Encequidar and Encequidar mesylate.

The modifier "about" should be considered as disclosing the range defined by the absolute values of the two endpoints. For example, the expression "from about 2 to about 4" also discloses the range "from 2 to 4." When used to modify a single number, the term "about" may refer to plus or minus 10% of the indicated number and includes the indicated number. For example, "about 10%" may indicate a range of 9% to 11%, and "about 1" means from 0.9-1.1.

As used herein, unless stated otherwise, PXRD peaks reported herein are preferably measured using $CuK_{\alpha}$ radiation, λ=1.54187 Å.

As used herein, unless stated otherwise, $^{13}C$ NMR reported herein are measured at 125 MHz at a magic angle spinning frequency $\omega_r/2\pi$=15 kHz, preferably at a temperature of at 293 K±3KC.

As used herein, unless stated otherwise, solid state FT-IR reported herein are measured at ATR in a spectral range 4000-550 $cm^{-1}$ at 293 K±3K.

As used herein, the term "isolated" in reference to solid state forms of Encequidar mesylate are physically separated from the reaction mixture in which it is formed.

A thing, e.g., a reaction mixture, may be characterized herein as being at, or allowed to come to "room temperature", often abbreviated "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C. A process or step may be referred to herein as being carried out "overnight." This refers to a time interval, e.g., for the process or step, that spans the time during the night, when that process or step may not be actively observed. This time interval is from about 8 to about 20 hours, or about 10 to about 18 hours, typically about 16 hours.

The term "solvate", as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

The amount of solvent employed in a chemical process, e.g., a reaction or a crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding methyl tert-butyl ether (MTBE) (1.5 v/v) to a 100 ml reaction mixture would indicate that 150 mL of MTBE was added.

As used herein, the term "reduced pressure" refers to a pressure of about 10 mbar to about 50 mbar.

The present disclosure includes solid state forms of Encequidar.

The present disclosure further includes a crystalline form of Encequidar designated as Form IV. Encequidar Form IV can be characterized by data selected from one or more of the following: a PXRD pattern having peaks at 4.1, 8.1, 12.2, 16.2 and 26.2 degrees 2-theta±0.2 degrees 2-theta; a PXRD pattern as depicted in FIG. 4; or combinations of these data.

Encequidar Form IV may be further characterized by a PXRD pattern having peaks at 4.1, 8.1, 12.2, 16.2 and 26.2 degrees 2-theta±0.2 degrees 2-theta, and also having one, two, three, four or five additional peaks at 8.8, 15.7, 19.5, 20.4 and 25.2 degrees 2-theta±0.2 degrees 2-theta.

Encequidar Form IV may alternatively be characterized by a PXRD pattern having peaks at 4.1, 8.1, 8.8, 12.2, 15.7, 16.2, 19.5, 20.4, 25.2 and 26.2 degrees 2-theta±0.2 degrees 2-theta.

Encequidar Form IV may be characterized by each of the above characteristics alone or by all possible combinations, e.g., by a PXRD pattern having peaks at 4.1, 8.1, 12.2, 16.2 and 26.2 degrees 2-theta±0.2 degrees 2-theta and/or a PXRD pattern as depicted in FIG. 4.

The present disclosure includes solid state forms of Encequidar mesylate.

The present disclosure further includes a crystalline form of Encequidar mesylate designated as Form K. Form K of Encequidar mesylate can be characterized by data selected from one or more of the following: a PXRD pattern having peaks at 6.0, 6.7, 10.4, 16.3 and 17.1 degrees 2-theta±0.2 degrees 2-theta; a PXRD pattern as depicted, or substantially as depicted, in FIG. 1; a PXRD pattern as depicted, or substantially as depicted, in FIG. 5, a FT-IR spectrum having peaks at 1689, 1652, 1463, 1416, 1383, 1118, 1037, 1003, 806 and 762 $cm^{-1}$±4 $cm^{-1}$; a FT-IR spectrum substantially as depicted in FIG. 6; or combinations of these data.

Form K of Encequidar mesylate may be further characterized by a PXRD pattern having peaks at 6.0, 6.7, 10.4, 16.3 and 17.1 degrees 2-theta±0.2 degrees 2-theta, and also having one, two, three, four, five or six additional peaks at 5.3, 8.9, 10.9, 20.8, 21.4 and 23.9 degrees 2-theta±0.2 degrees 2-theta.

Form K of Encequidar mesylate may alternatively be characterized by a FT-IR spectrum having peaks at 2839, 1689, 1652, 1620, 1539, 1521, 1484, 1463, 1416, 1383, 1331, 1223, 1158, 1118, 1037, 1003, 981, 961, 872, 838, 806, 776, 762, 748, 586 $cm^{-1}$±4 $cm^{-1}$.

Form K of Encequidar mesylate may alternatively or additionally be characterized by a solid state $^{13}C$ NMR spectrum with characteristic peaks at 177.4, 163.1, 154.8, 134.4 and 110.7 ppm±0.2 ppm; and/or a solid state $^{13}C$ NMR spectrum having the following chemical shift absolute differences from reference peak at 102.1 ppm±1 ppm: 75.3, 60.9, 52.7, 32.2 and 8.5 ppm±0.1 ppm.

Crystalline Form K of Encequidar mesylate may be characterized by a solid state $^{13}C$ NMR having the following full peak list: 177.4, 163.1, 154.8, 147.6, 144.3, 140.8, 134.4, 131.1, 129.4, 126.9, 124.6, 123.4, 121.0, 118.8, 110.7, 108.2, 104.9, 102.1, 55.4, 50.6, 39.3, 29.9, 26.1 and 20.5 ppm±0.2 ppm; a $^{13}C$ NMR spectrum substantially as depicted in FIG. 7, FIG. 8 or FIG. 9; or combinations of these data.

Form K of Encequidar mesylate may alternatively be characterized by a PXRD pattern having peaks at 5.3, 6.0, 6.7, 8.9, 10.4, 10.9, 16.3, 17.1, 20.8, 21.4 and 23.9 degrees 2-theta±0.2 degrees 2-theta.

Form K of Encequidar mesylate may be characterized by each of the above characteristics alone or by all possible combinations, e.g., by a PXRD pattern having peaks at 6.0, 6.7, 10.4, 16.3 and 17.1 degrees 2-theta±0.2 degrees 2-theta, a PXRD pattern as depicted in FIG. 1, and/or a PXRD pattern as depicted in FIG. 5.

Accordingly, crystalline Form K of Encequidar mesylate, may be characterized by data selected from one or more of the following: (a) a PXRD pattern having peaks at 6.0, 6.7, 10.4, 16.3 and 17.1 degrees 2-theta±0.2 degrees 2-theta; (b) a PXRD pattern substantially as depicted in FIG. 1 or FIG. 5; (c) a FT-IR spectrum having peaks at 1689, 1652, 1463, 1416, 1383, 1118, 1037, 1003, 806 and 762 $cm^{-1}$±4 $cm^{-1}$; (d) an FT-IR spectrum substantially as depicted in FIG. 6; (e) a solid state $^{13}C$ NMR spectrum having characteristic peaks in the range of 100-200 ppm at: 177.4, 163.1, 154.8, 134.4 and 110.7 ppm±0.2 ppm; (f) a solid state $^{13}C$ NMR spectrum having the following chemical shift absolute differences from a reference peak at 102.1 ppm±1 ppm: 75.3, 60.9, 52.7, 32.2 and 8.5 ppm±0.1 ppm; (g) a solid state $^{13}C$ NMR having peaks in the range of 0-200 ppm at: 177.4, 163.1, 154.8, 147.6, 144.3, 140.8, 134.4, 131.1, 129.4, 126.9, 124.6, 123.4, 121.0, 118.8, 110.7, 108.2, 104.9, 102.1, 55.4, 50.6, 39.3, 29.9, 26.1 and 20.5 ppm±0.2 ppm; (h) a solid state $^{13}C$ NMR spectrum substantially as depicted in FIG. 7, FIG. 8 or FIG. 9; or (i) combinations of these data. Thus, crystalline Form K of Encequidar mesylate may be characterized by any of the following combinations: (a) and any one of: (c), (d), (e), (f), (g), or (h); (b) and any one of: (c), (d), (e), (f), (g), or (h); (c) and any one of: (e), (f), (g), or (h); (d) and any one of: (e), (f), (g), or (h). The crystalline Form K of Encequidar mesylate may alternatively be characterized by a PXRD pattern having peaks at 6.0, 6.7, 10.4, 16.3 and 17.1 degrees 2-theta±0.2 degrees 2-theta, and also having one, two, three, four, five or six additional peaks at 5.3, 8.9, 10.9, 20.8, 21.4 and 23.9 degrees 2-theta±0.2 degrees 2-theta and any one of: (c), (d), (e), (f), (g), or (h). Alternatively, the crystalline Form K of Encequidar mesylate may be characterised by a PXRD having peaks at 5.3, 6.0, 6.7, 8.9, 10.4, 10.9, 16.3, 17.1, 20.8, 21.4 and 23.9 degrees 2-theta±0.2 degrees 2-theta and any one of: (c), (d), (e), (f), (g), or (h).

The present disclosure further includes a crystalline form of Encequidar mesylate designated as Form L. Form L of Encequidar mesylate can be characterized by data selected from one or more of the following: a PXRD pattern having peaks at 5.1, 7.5, 9.0, 10.2 and 15.2 degrees 2-theta±0.2 degrees 2-theta and missing peaks at about 7.0, 11.0 and 17.5 degrees 2-theta±0.2 degrees 2-theta; a PXRD pattern as depicted in FIG. 2; or combinations of these data.

Form L of Encequidar mesylate may be further characterized by a PXRD pattern having peaks at 5.1, 7.5, 9.0, 10.2 and 15.2 degrees two theta±0.2 degrees 2-theta, and missing peaks at about 7.0, 11.0 and 17.5 degrees 2-theta±0.2 degrees 2-theta, and also having one, two, three, four or five additional peaks at 6.1, 6.6, 22.3, 24.8 and 25.8 degrees 2-theta±0.2 degrees 2-theta.

Form L of Encequidar mesylate may alternatively be characterized by a PXRD pattern having peaks at 5.1, 6.1, 6.6, 7.5, 9.0, 10.2, 15.2, 22.3, 24.8 and 25.8 degrees 2-theta±0.2 degrees 2-theta and missing peaks at about 7.0, 11.0 and 17.5 degrees 2-theta±0.2 degrees 2-theta.

Encequidar mesylate Form L may be an anhydrous form.

Form L of Encequidar mesylate may be characterized by each of the above characteristics alone/or by all possible combinations, e.g., by a PXRD pattern having peaks at 5.1, 7.5, 9.0, 10.2 and 15.2 degrees 2-theta±0.2 degrees 2-theta and missing peaks at about 7.0, 11.0 and 17.5 degrees 2-theta±0.2 degrees 2-theta; and a PXRD pattern as depicted in FIG. 2.

The present disclosure further includes a crystalline form of Encequidar mesylate designated as Form M. Encequidar mesylate Form M can be characterized by data selected from one or more of the following: a PXRD pattern having peaks at 5.2, 7.4, 8.4, 12.6 and 13.6 degrees 2-theta±0.2 degrees 2-theta; a PXRD pattern as depicted in FIG. 3; or combinations of these data.

Encequidar mesylate Form M may be further characterized by a PXRD pattern having peaks at 5.2, 7.4, 8.4, 12.6 and 13.6 degrees 2-theta±0.2 degrees 2-theta, and also having one, two, three, four or five additional peaks at 6.6, 7.7, 10.4, 10.9 and 16.2 degrees 2-theta±0.2 degrees 2-theta.

Encequidar mesylate Form M may alternatively be characterized by a PXRD pattern having peaks at 5.2, 6.6, 7.4, 7.7, 8.4, 10.4, 10.9, 12.6, 13.6 and 16.2 degrees 2-theta±0.2 degrees 2-theta.

Encequidar mesylate Form M may be characterized by each of the above characteristics alone or by all possible combinations, e.g., by a PXRD pattern having peaks at 5.2, 7.4, 8.4, 12.6 and 13.6 degrees 2-theta±0.2 degrees 2-theta and/or a PXRD pattern as depicted in FIG. 3.

The present disclosure also provides the use of the solid state forms of Encequidar and Encequidar mesylate of the present disclosure for preparing different solid state forms of Encequidar and Encequidar Mesylate, such as amorphous Encequidar and Encequidar or other crystalline forms of Encequidar and Encequidar Mesylate. For example, the present disclosure provides the use of Encequidar mesylate Form K of the present disclosure for preparing different solid state forms of Encequidar and Encequidar Mesylate, particularly for preparing Encequidar mesylate Form L. In addition, the present disclosure provides the use of Encequidar mesylate Form M of the present disclosure for preparing different solid state forms of Encequidar and Encequidar Mesylate, particularly for preparing Encequidar mesylate Form K and/or Form L.

The present disclosure further encompasses processes for preparing solid state forms of Encequidar and Encequidar mesylate of the present disclosure. The disclosure further includes processes for preparing different solid state forms of Encequidar and Encequidar mesylate. The process includes preparing at least one of the solid state forms of Encequidar and Encequidar mesylate of the present disclosure, and converting it to different solid state forms of Encequidar and Encequidar mesylate.

In another embodiment the present disclosure encompasses the above solid state forms Encequidar and Encequidar mesylate for use in the preparation of pharmaceutical compositions and/or formulations, in some embodiments for the treatment of cancer, or in some embodiments for the treatment of metastatic breast cancer and/or gastric cancer. The said pharmaceutical compositions and/or formulations can be as a combination with additional active agents, such as Paclitaxel.

In another embodiment the present disclosure encompasses the use of the above described solid state forms of Encequidar and Encequidar mesylate for the preparation of pharmaceutical compositions and/or formulations, particularly as a combination with additional active agents, such as Paclitaxel.

The present disclosure further provides pharmaceutical compositions including solid state forms of Encequidar and Encequidar mesylate of the present disclosure. In some embodiments, the said pharmaceutical compositions is a combination with additional active agents, such as Paclitaxel.

In yet another embodiment, the present disclosure encompasses pharmaceutical formulations including solid state forms of Encequidar and Encequidar mesylate of the present disclosure, and at least one pharmaceutically acceptable excipient. In particular embodiments, the said pharmaceutical compositions is a combination with additional active agents, such as Paclitaxel.

Pharmaceutical formulations of the present disclosure contain any one or a combination of the solid state forms of Encequidar and Encequidar mesylate of the present disclosure. In addition to the active ingredient, the pharmaceutical formulations of the present disclosure can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g., Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g., Ac-Di-Sol®, Primellose®), colloidal silicon dioxide, croscarmellose sodium, crospovidone (e.g., Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g., Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present disclosure include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present disclosure, the active ingredient and any other solid excipients may be dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present disclosure include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present disclosure can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present disclosure include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, in embodiments the route of administration is oral.

The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present disclosure can be a capsule containing the composition, such as a powdered or granulated solid composition of the disclosure, within either a hard or soft shell. The shell can be made from gelatin and optionally contain a plasticizer such as glycerin and sorbitol, and an opacifying agent or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present disclosure can include any of the aforementioned blends and granulates that were described with reference to tableting, but they are not subjected to a final tableting step.

In embodiments, a pharmaceutical formulation of Encequidar and Encequidar mesylate is formulated for administration to a mammal, such as a human. Encequidar and Encequidar mesylate can be formulated, for example, as a viscous liquid solution or suspension, such as a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The present disclosure encompasses a process to prepare said formulations of solid state forms of Encequidar and Encequidar mesylate thereof by combining the solid state forms of Encequidar and Encequidar mesylate according to the present disclosure and at least one pharmaceutically acceptable excipient. The process can further include adding additional active agent, such as Paclitaxel.

Solid state forms of Encequidar and Encequidar mesylate as defined herein, as well as the pharmaceutical compositions or formulations of Encequidar and Encequidar mesylate can be used as medicaments, in some embodiments for the treatment of cancer, or in some embodiments for the treatment of metastatic breast cancer and gastric cancer. In particular, it is used as a combination with additional active agents, such as Paclitaxel.

The present disclosure also provides a method of treating cancer, or a method of treating metastatic breast cancer and gastric cancer, by administering a therapeutically effective amount of any one or a combination of the solid state forms of Encequidar and Encequidar mesylate prepared according to the present disclosure, or at least one of the above pharmaceutical compositions or formulations, optionally in a form of a combination with additional active agents, such as Paclitaxel, to a subject suffering from cancer or to a subject suffering from metastatic breast cancer and/or gastric cancer, or otherwise in need of the treatment.

The present disclosure also provides the use of solid state forms of Encequidar and Encequidar mesylate, or at least one of the above pharmaceutical compositions or formulations for the manufacture of a medicament for treating cancer or for the manufacture of a medicament for treating metastatic breast cancer and/or gastric cancer. Optionally, the medicament is a combination with additional active agents, such as Paclitaxel.

Having described the solid state forms of Encequidar and Encequidar mesylate with reference to certain exemplary embodiments, other embodiments will become apparent to one skilled in the art from consideration of the specification. The disclosure is further illustrated by reference to the following examples describing in detail the preparation of the composition and methods of use of the disclosure. It will be apparent to those skilled in the art that many modifications, both to materials and methods, may be practiced without departing from the scope of the disclosure.

Analytical Methods

Powder X-Ray Diffraction Pattern ("PXRD") Method:

Sample was powdered in mortar and pestle and applied directly on silicon plate holder. The X-ray powder diffraction pattern was measured with an X-Ray powder diffractometer PanAlytical X'pert Pro; equipped with CuKα radiation (λ=1.54187 Å); X'Celerator detector with active length 2.122 degrees 2-theta; laboratory temperature 25±3° C.; zero background sample holders. Scanning parameters: angle range: 3-40 deg., step size 0.0167, time per step 42 seconds, continuous scan, with spin (60 rpm).

FT-IR Method:

Sample was powdered in mortar and pestle and applied directly on ATR crystal placed in FTIR spectrometer. Prior to the measurement, background was determined and used for the sample correction. The conditions used for the measurement are following:

Equipment: Nicolet 380 FT-IR Spectrometer
Mode: ATR;
Spectral range: 4000-550 $cm^{-1}$;
Sample gain: 1.0;
Number of scans: 64;
Resolution: 4.0 $cm^{-1}$
Temperature: 293 K±3K.

ssNMR Method:

$^{13}C$ CP/MAS NMR spectra were measured at 125 MHz using Bruker Avance III 500 WB/US NMR spectrometer (Karlsruhe, Germany, 2003) at magic angle spinning (MAS)

frequency $\omega_r/2\pi$=15 kHz. In all cases finely powdered samples were placed into 4-mm $ZrO_2$ rotors and the standard "cpmas" pulseprogram was used. During acquisition of the data the high-power dipolar decoupling "TPPM" (two-pulse phase-modulated) was applied. The flip-pulse length was 4.8 s. Applied nutation frequency of $B_1(^1H)$ field was frequency $\omega_r/2\pi$=89.3 kHz. Nutation frequency of $B_1(^{13}C)$ and $B_1(^1H)$ fields during cross-polarization was $\omega_r/2\pi$=62.5 kHz. The number of scans was 4096, repetition delay was 4.0 s. Taking into account frictional heating of the samples during fast rotation all NMR experiments were performed at 293 K (precise temperature calibration was performed). The NMR spectrometer was completely calibrated and all experimental parameters were carefully optimized prior the investigation of samples. Magic angle was set using KBr during standard optimization procedure and homogeneity of magnetic field was optimized using adamantane sample (resulting line-width at half-height $\Delta\nu_{1/2}$ was less than 3.5 Hz at 250 ms of acquisition time).

EXAMPLES

Preparation of Starting Material

Encequidar and Encequidar mesylate can be prepared according to any procedure known in the art, for example the procedures described in International Publication No. WO 2005/033097 or in International Publication No. WO 2011/087316.

Example 1: Preparation of Encequidar Mesylate Form K

Encequidar base (0.5 grams) was suspended in 10 mL MeOH (99%) and heated up to 50° C. during 30 minutes. 0.054 ml of methanesulfonic acid was added. A clear solution was obtained while stirring at 50° C. for 10 minutes. Subsequently, the clear solution was cooled from 50° C. to 10° C. during 120 minutes. The solution was kept at 10° C. for 4 hours under stirring, while the solution gradually begins to be cloudy. The cloudy solution was kept overnight at RT in the reactor under stirring. The slurry was filtrated to obtain wet crystals which were left on the filter for about 60 minutes. The sample was dried for 8 hours at 50° C. under Nitrogen. PXRD measurement confirmed Encequidar mesylate Form K (FIG. 1).

The wet crystals were also measured by PXRD to obtain Form M, characterized by PXRD pattern in FIG. 3.

Example 2: Preparation of Encequidar Mesylate Form L

Form K obtained by Example 1 was left for drying on the filter under Nitrogen stream for 30 minutes and further dried at 75° C. for 10 hours under stream of Nitrogen. PXRD measurement confirmed Encequidar mesylate Form L (FIG. 2).

Example 3: Preparation of Encequidar Form IV

Encequidar free base (89 grams) was dissolved in mixture of toluene (900 mL) and methanol (300 mL) heated to boiling temperature of about 62-64° C. The solution was filtered (hot filtration) and the filtrate was diluted with methanol (300 mL, at room temperature). Obtained mixture was heated again to boiling temperature (about 62-64° C.) and then it was cooled to 17° C. (jacket temperature) during 1 hour (spontaneous crystallization started at about 30° C.). After 1 hour stirring at about 17° C., insoluble solid was separated by filtration, washed with methanol (about 400 mL) and dried at room temperature with nitrogen blowing-through material on the filter for overnight to obtain Encequidar Form IV, described by PXRD in FIG. 4 (73 grams).

Example 4: Preparation of Encequidar Mesylate Form K

Encequidar mesylate (27.5 grams) was suspended in 99% solution of methanol-water (99% methanol and 1% water, 540 ml), and heated up to 65° C. during 45 minutes to obtain a clear solution. The clear solution was cooled down to 40° C. for about 30 minutes, and seeding with Encequidar mesylate Form K (500 mg) was added at this temperature. The obtained suspension was stirred at temperature 40° C. for about 30 minutes, then cooled down to 10° C. during 2 hours and kept further for about 5 hours at 10° C., under stirring. The obtained wet crystals were filtered and washed by 99% solution of methanol-water (50 ml), left for 45 minutes on the filter under Nitrogen stream and then dried under stream of Nitrogen at 50° C. for about 5 hours. PXRD measurement confirmed Encequidar mesylate form K content, as described in FIG. 5.

Example 5: Preparation of Encequidar Mesylate Form L

Form M (wet crystals) obtained by Example 1 was left to dry on the filter under a nitrogen stream for 30 minutes, and further dried at 75° C. for 10 hours under a stream of nitrogen. PXRD measurement confirmed Encequidar mesylate Form L as per FIG. 2.

The invention claimed is:

1. A crystalline form of Encequidar mesylate, characterized by a PXRD pattern having peaks at 6.0, 6.7, 10.4, 16.3 and 17.1 degrees 2-theta±0.2 degrees 2-theta.

2. The crystalline form of Encequidar mesylate according to claim 1, characterized by a PXRD pattern also having one, two, three, four, five or six additional peaks at 5.3, 8.9, 10.9, 20.8, 21.4 and 23.9 degrees 2-theta±0.2 degrees 2-theta.

3. The crystalline form of Encequidar mesylate according to claim 1, which is further characterized by a FT-IR spectrum having peaks at 2839, 1689, 1652, 1620, 1539, 1521, 1484, 1463, 1416, 1383, 1331, 1223, 1158, 1118, 1037, 1003, 981, 961, 872, 838, 806, 776, 762, 748, 586 $cm^{-1}$±4 $cm^{-1}$.

4. The crystalline form of Encequidar mesylate according to claim 1, which is further characterized by an FT-IR spectrum having peaks at 1689, 1652, 1463, 1416, 1383, 1118, 1037, 1003, 806 and 762 $cm^{-1}$±4 $cm^{-1}$.

5. The crystalline form of Encequidar mesylate according to claim 1, which is further characterized by data selected from:

(i) a solid state $^{13}C$ NMR spectrum having characteristic peaks in the range of 100-200 ppm at: 177.4, 163.1, 154.8, 134.4 and 110.7 ppm 0.2 ppm;

(ii) a solid state $^{13}C$ NMR spectrum having the following chemical shift absolute differences from a reference peak at 102.1 ppm±1 ppm: 75.3, 60.9, 52.7, 32.2 and 8.5 ppm±0.1 ppm; or (iii) a solid state $^{13}C$ NMR having peaks in the range of 0-200 ppm at: 177.4, 163.1, 154.8, 147.6, 144.3, 140.8, 134.4, 131.1, 129.4, 126.9, 124.6, 123.4, 121.0, 118.8, 110.7, 108.2, 104.9, 102.1, 55.4, 50.6, 39.3, 29.9, 26.1 and 20.5 ppm±0.2 ppm.

6. The crystalline form of Encequidar mesylate according to claim 1, which contains no more than 20% of any other crystalline forms of Encequidar mesylate.

7. The crystalline form of Encequidar mesylate according to claim 1, which contains no more than 20% of amorphous Encequidar mesylate.

8. A pharmaceutical composition comprising the crystalline form of Encequidar mesylate according to claim 1.

9. A process for preparing a pharmaceutical formulation comprising combining the crystalline form of Encequidar mesylate according to claim 1 with at least one pharmaceutically acceptable excipient.

10. A medicament comprising the crystalline form of Encequidar mesylate according to claim 1.

11. A method of treating cancer, comprising administering a therapeutically effective amount of the crystalline form of Encequidar mesylate according to claim 1 to a subject in need of the treatment.

12. A process for preparing an Encequidar salt, co-crystal, or a solid state form thereof comprising preparing the crystalline form of Encequidar mesylate according to claim 1, and converting it to another Encequidar salt, co-crystal or a solid state form thereof.

13. The process according to claim 9, wherein the pharmaceutical formulation is a solid dispersion.

* * * * *